United States Patent [19]

Miller

[11] Patent Number: 5,263,931
[45] Date of Patent: Nov. 23, 1993

[54] BALLOON CATHETER FOR DILATING A PROSTATIC URETHRA

[75] Inventor: Gary H. Miller, Milpitas, Calif.

[73] Assignee: Advanced Cardiovascular Systems, Inc., Santa Clara, Calif.

[21] Appl. No.: 908,939

[22] Filed: Jul. 6, 1992

Related U.S. Application Data

[63] Continuation of Ser. No. 483,397, Feb. 14, 1990, abandoned.

[51] Int. Cl.⁵ ............................................. A61M 29/02
[52] U.S. Cl. ...................................... 604/96; 606/192
[58] Field of Search ............................ 606/191–197; 604/96–103; 128/4–6

[56] References Cited

U.S. PATENT DOCUMENTS

| | | | |
|---|---|---|---|
| 550,238 | 11/1895 | Allen | 604/102 |
| 2,642,874 | 6/1953 | Keeling | 128/349 |
| 2,833,003 | 9/1974 | Taricco | 128/347 |
| 2,849,002 | 3/1956 | Oddo | 128/325 |
| 3,977,408 | 8/1976 | MacKew | 128/349 |
| 4,205,691 | 6/1980 | Patel | 128/774 |
| 4,219,026 | 8/1980 | Layton | 128/325 |
| 4,660,560 | 4/1987 | Klein | 128/344 |
| 4,762,128 | 8/1988 | Rosenbluth | 128/343 |
| 4,793,350 | 12/1988 | Mar et al. | 604/96 |
| 4,896,670 | 1/1990 | Crittenden | 604/96 |
| 4,917,088 | 4/1990 | Crittenden | 604/96 |
| 4,964,409 | 10/1990 | Tremulis | 128/657 |
| 5,071,429 | 12/1991 | Pinchuk et al. | 606/192 |

FOREIGN PATENT DOCUMENTS 345051 12/1989 European Pat. Off. .

OTHER PUBLICATIONS

*Urological International* 2, pp. 158-171, 1956 Deisting, W. "Transurethral Dilatation of the Prostate".
Urologic *Radiology 2*, pp. 33-37, 1980 Russinovich et al, "Balloon Dilatation of Urethral Strictures".
*Radiology* 152, pp. 655-657, 1984 Burhenne et al "Prostatic Hyperplasia: Radiological Intervention".
Urologic Clinics of North America vol. 15, No. 3, pp. 529-535 Aug. 1988 Reddy et al "Balloon Dilatation of the Porostate for Treatment of Benign Hyperplasia".
*Radiology* 152 pp. 57-58, 1985 Quinn et al "Balloon Dilatation of the Prostatic Urethra".

*Primary Examiner*—Stephen C. Pellegrino
*Assistant Examiner*—William Lewis
*Attorney, Agent, or Firm*—Dykema Gossett

[57] ABSTRACT

A catheter system for dilating the prostatic urethra of a male patient. The catheter has an elongated tubular catheter body with an inner lumen extending therein, an inflatable relatively inelastic balloon on the distal extremity of the catheter body, a core member extending through the balloon interior and at least to and preferably out the distal end of the catheter body where a flexible body such as a helical coil is disposed about and secured thereto. The catheter body proximal to the balloon has a diameter which is sufficiently small to allow the catheter shaft to be slidably disposed within the working channel of a flexible cystoscope. The flexible cystoscope can be utilized to allow the physician performing the dilatation to observe the external sphincter to ensure that there is no dilation thereof.

4 Claims, 2 Drawing Sheets

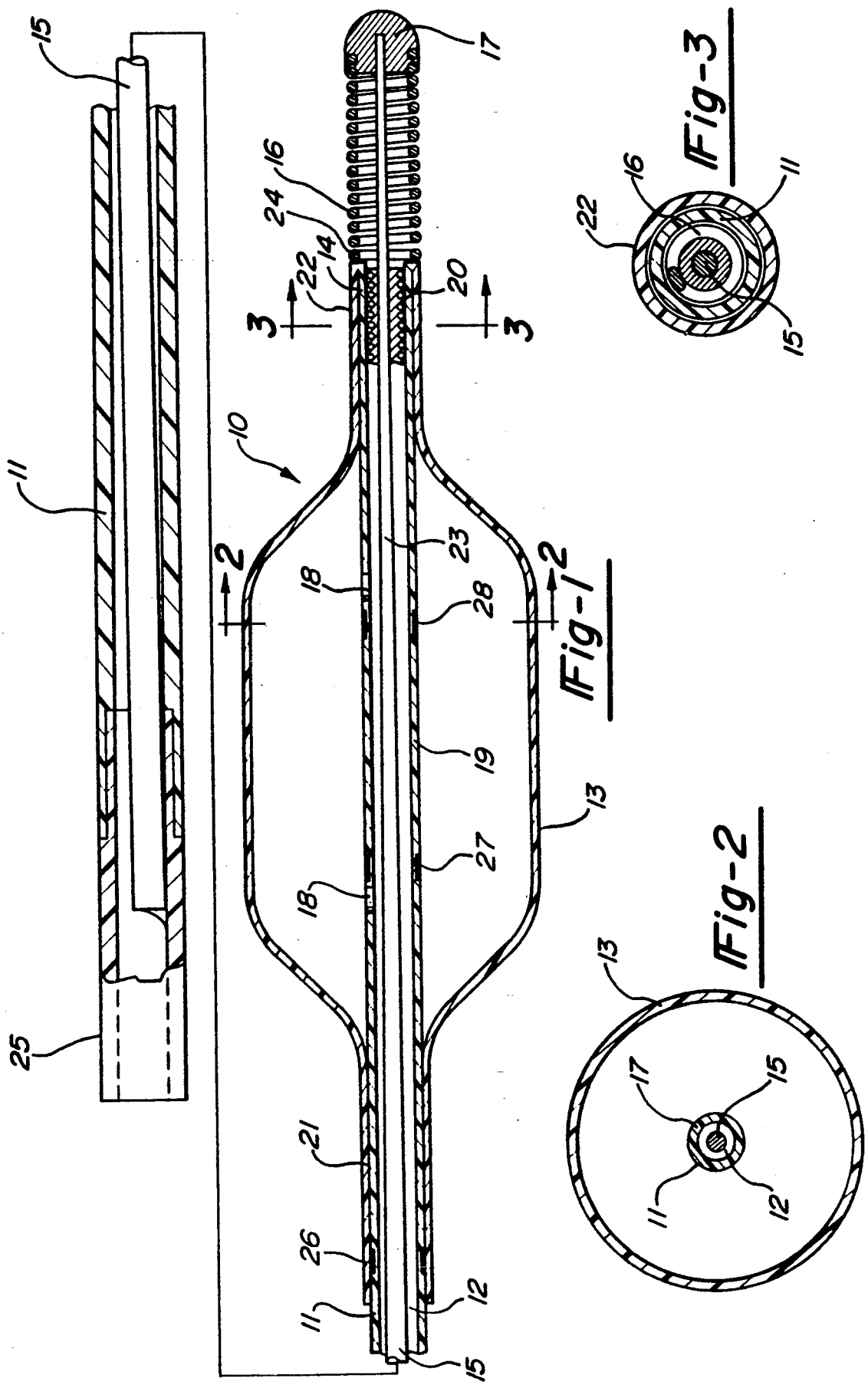

BALLOON CATHETER FOR DILATING A PROSTATIC URETHRA

This is a continuation of the application Ser. No. 07/483,397 which was filed on Feb. 14, 1990 now abandoned.

BACKGROUND OF THE INVENTION

This invention generally relates to a balloon catheter system and method for dilating a prostatic urethra.

Dilatation of the prostatic urethra to eliminate or minimize urethral blockage has been considered for many years. For example, Guthry in 1830, Civale in 1841, Mercier in 1850 and Kramer in 1910 all developed metal dilators to unblock urethral obstructions. A good description of the early work in this area can be found in Hinman, F., Jr. (Ed.) *Benign Prostatic Hypertrophy*, Chapter 5, Springer-Valag, 1983. Russinovich et al. utilized a balloon dilatation catheter which was developed for angioplasty by Grüntzig et al. in the late 1970s to successfully dilate the prostatic urethra of several male patients which has been partially occluded (*Urologic-Radiology*, 2, 33–37, 1980).

Balloon catheters for dilating occluded prostatic urethras are commercially available. They are very similar to the dilatation catheters utilized for valvuloplasty procedures, except that the catheter shafts are much shorter.

In typical prostatic dilatation procedures, a guiding catheter is first introduced through the patient's urethra into the bladder so that retrograde urethrography can be performed to outline the external sphincter and then a flexible guidewire is advanced through the guiding catheter into the patient's bladder. The balloon dilatation catheter is advanced over the guidewire until the balloon thereof is located within the patient's prostatic urethra where it would be inflated to an elevated pressure, usually above 2 atmospheres, to dilate the prostatic urethra and the surrounding prostate gland. A cystoscope is employed in this procedure to observe the placement of the dilatation catheter and the dilatation procedures as well as to examine of the urethra both before and after the procedure.

The dilatation catheters presently employed for prostatic dilatations generally have relatively large profiles which makes advancement and accurate placement thereof very difficult. Commercially available catheters have much too large a profile to be advanced through the lumen or working channel of a cystoscope particularly a flexible cystoscope which has a very small working channel.

What has been needed and heretofore unavailable is a dilatation catheter which is suitable for prostatic dilatations but which has a sufficiently low profile to pass through the working channel or lumen of a cystoscope. The present invention satisfies that need.

SUMMARY OF THE INVENTION

This invention is directed to the dilatation of the prostatic urethral canal of a male patient and to a catheter system specifically designed for such use.

The dilatation catheter of the invention includes an elongated catheter body with proximal and distal portions and an inner lumen extending therein, an inflatable balloon on the distal portion of the tubular body, a core member extending through the catheter body and balloon interior. Preferably, the core member extends out the distal end of the catheter body, and a flexible member is disposed about and secured to the portion of the core member which extends out of the distal end of the catheter body to minimize any trauma to the wall of the urethra as the catheter passes therethrough. Preferably, the flexible body is a helical coil. The inner lumen of the catheter body is in fluid communication with the interior of the inflatable balloon and means are provided on the proximal end of the catheter body to direct inflation fluid through the inner lumen to the interior of the balloon.

The dilatation catheter of the invention is advanced through the patient's urethral canal until the balloon thereof is disposed within the patient's prostatic urethra and the coil on the distal end of the catheter extends into the patient's bladder. Upon inflation of the balloon, the prostatic urethra and the surrounding prostate gland are dilated resulting in increased fluid flow therethrough.

The catheter of the invention is particularly suitable for use as a catheter system in conjunction with a cystoscope and has a sufficiently low shaft profile to be slidable within the working channel of the cystoscope. The catheter can be used to guide the cystoscope to a desired location within the patient's urethra. It is particularly advantageous to locate the distal tip of the cystoscope adjacent the external sphincter of the patient so that it can be observed through the eyepiece at the proximal end of the cystoscope while the balloon is inflated to ensure that there is no dilatation of the external sphincter. The cystoscope, of course, can be utilized to examine the entire urethral canal prior to and after the dilatation procedure if desired.

The shaft of the catheter of the invention has a diameter less than about 4 mm, preferably less than 3 mm which is considerably smaller than the shaft diameters of presently available catheters used to dilate prostatic urethra. Generally, the inflated diameter of the balloon exceeds 10 mm and preferably ranges from about 15 to about 50 mm.

The balloon is made of flexible but relatively inelastic plastic material, such as biaxially oriented polyethylene or polyethylene terephthalate, so that it can be inflated with inflation liquid to a predetermined size and shape to effectively and safely dilate the prostatic urethra and the surrounding prostate gland in a controlled manner.

After dilating the prostatic urethral canal, the catheter may be further advanced until the balloon is disposed within the bladder so that the cystoscope can be advanced over the dilatation catheter through the prostatic urethra to inspect this area and determine the extent of the dilation and whether injury to the urethral wall has occurred. These and other advantages of the invention will become more apparent from the following detailed description thereof when taken in conjunction with the accompanying exemplary drawings.

BRIEF DESCRIPTION OF THE DRAWINGS

FIG. 1 is a elevational view in section of a balloon dilatation catheter embodying features of the invention.

FIG. 2 is a transverse cross-sectional view taken along the lines 2—2 shown in FIG. 1;

FIG. 3 is a transverse cross-sectional view taken along the line 3—3 as shown in FIG. 1.

DETAILED DESCRIPTION OF THE INVENTION

Figure 4:
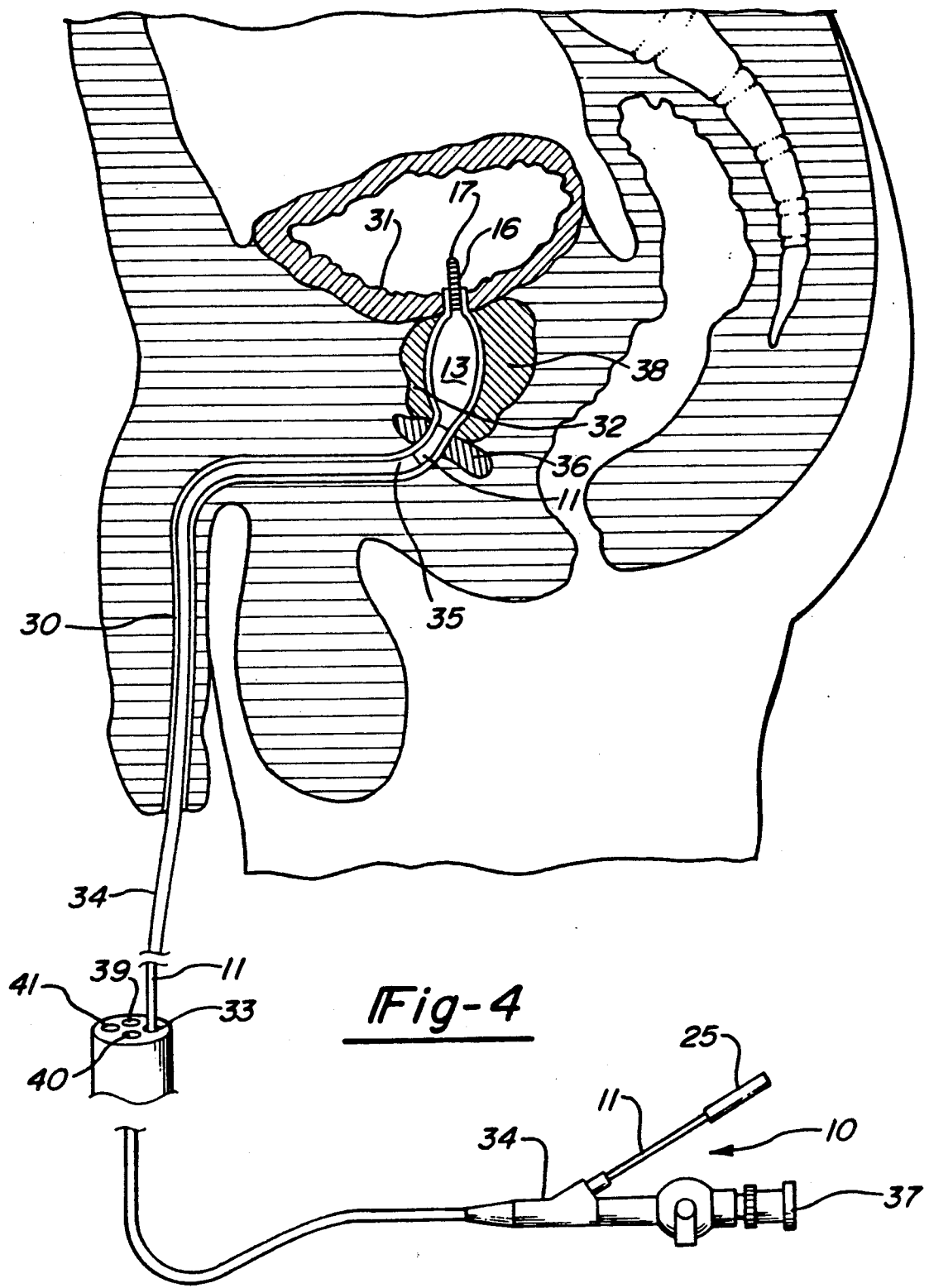
FIG. 4 is a diagrammatic view of a male patient's urethra illustrating the dilation of the prostatic urethra thereof with the catheter shown in FIG. 1.

FIGS. 1-3 illustrate a balloon dilatation catheter 10 which embodies features of the invention. The catheter 10 includes an elongated catheter body 11 having an inner lumen 12, an inflatable, relatively inelastic balloon 13 secured to the catheter body 11 adjacent the distal end 14 thereof, and a core member 15 which extends through the inner lumen of the catheter body and out the distal end thereof. A helical coil 16 is disposed about the portion of the core member 15 which extends out the distal end 14 of the catheter body 11 and is secured to the rounded plug 17 at the distal end of the core member 15. The inner lumen 12 of the catheter body 11 is in fluid communication with the interior of the inflatable balloon 13 through inflation ports 18 provided in the wall 19 of the catheter body 11. An intermediate coil 20 is bonded (e.g., soldered) to the core member 15 at a location proximal to the plug 17 The distal end of the catheter body 11 is adhesively bonded to the intermediate coil 20.

The catheter body 11 is generally a tubular shaped member with an outer diameter of about 0.035 to about 0.065 inch (0.889-1.651 mm), an inner diameter of about 0.01 to about 0.05 inch (0.254-1.27 mm) and a length usually less than 100 cm, preferably about 30 to about 80 cm. The catheter body 11 can be formed of suitable plastic materials such as polyethylene, polyester, or polyvinylchloride. The proximal portion of the catheter body can be made from hypotubing (stainless steel) to aid in the pushability of the catheter.

The balloon 13 is secured by suitable means such as an adhesive to the exterior of the catheter body 11 by the proximal skirt 21 and distal skirt 22 thereof. The inflatable balloon 13 is flexible but is formed of relatively inelastic material, such as polyethylene or polyethylene terephthalate, so that when it is filled with liquid it inflates in a controlled manner to a predetermined size and shape. The polyethylene terephthalate is preferably formed from a polymer resin with an intrinsic viscosity less than 1. The thin-walled balloon is typically about 2 to about 10 cm in length (including tapered ends) and has an inflated diameter of at least 10 mm, preferably about 15 to about 40 mm. The wall thickness in the working section (i.e., cylindrically shaped section) of the balloon 13 is about 0.0005 to about 0.005 inch (0.013-0.127 mm).

The core member 15 which extends through the inner lumen 12 of the catheter body 11 has a distal portion 23 which is tapered distally in one or more steps or continuously to increase the flexibility of the catheter. The outer diameter of the core member 15 proximal to the tapered distal portion 23 should be uniform and less than 0.04 inch (1.02 mm) preferably about 0.01 to about 0.03 inch (0.254-0.762 mm). The distal end 14 of the catheter body 11 is sealed about the portion of the core member 15 passing therethrough to fix the core member therein and to close off the distal end of the inner lumen 12 to prevent loss of inflation fluid therethrough.

The proximal end 24 of the helical coil 16 is suitably bonded (e.g., adhesively) to the distal end 14 of the catheter body 11. The distal end of the core member 15 is shown secured to the plug 17, but, if desired, the core member 15 can terminate short of the distal end of the coil 16 and a shaping ribbon (not shown) may extend from the core member to the rounded plug 17 to increase the flexibility of the distal tip of the catheter. The wire forming the coil 16 can be made from suitable material such as stainless steel with a diameter of about 0.001 to about 0.015 inch (0.025-0.38 mm), preferably about 0.007 inch (0.178 mm). The outer diameter of the coil 16 is essentially the same as the outer diameter of the catheter body 11. The length of the coil 16 can range from about 0.25 cm. Both the rounded plug 17 and the coil 16 can be made of suitable highly radiopaque materials to facilitate the fluoroscopic observation thereof when the catheter is positioned within a patient. In some embodiments it may be desireable to terminate the core member 15 at the distal end 14 of the catheter body.

The proximal end 24 of the elongated catheter body 11 is provided with an adapter 25 which allows inflation fluid to be introduced into the inner lumen 12 and ultimately be directed to the interior of the balloon 13 through port 18 in the tubular wall 19 of the catheter body 11. The adapter 25 as shown is a length of stainless steel hypotubing with the proximal end of the core member 15 suitably secured (e.g., by welding) to the inside thereof. Means are provided on the proximal end of the hypotube to facilitate the mounting of a syringe (not shown) or other suitable device to provide inflation fluid at high pressure. Typically fluid pressures in the range of 3 to 6 atmospheres are utilized for the dilatation procedure. However, greater or lesser pressures may be employed. To facilitate fluorscopic observation of the catheter radiopaque markers 26, 27 and 28 are provided on the catheter body 11.

In use, as shown in FIG. 4, the catheter 10 of the invention is advanced through the patient's urethral canal 30 until the flexible coil 16 extends into the patient's bladder 31 and the balloon 13 is disposed within the prostatic urethra 32. The proximal end of the catheter body 11 is backloaded into the working channel or lumen 33 of flexible cystoscope 34, and then the cystoscope 34 may be advanced over the in-place catheter 10 to a location proximately adjacent the exterior sphincter. In the alternative, the proximal end of the catheter body 11 can be backloaded into the cystoscope 34 and then both can be advanced together through the urethral canal 30. Preferably, the distal tip 35 of the cystoscope 34 is positioned adjacent the external sphincter 36 so that during the inflation of the balloon 13 the physician can observe the sphincter 36 through eyepiece 37 on the proximal end of cystoscope 34 to be sure that it is not being dilated. In this procedure, the balloon 13 is inflated with preferably radiopaque liquid to provide an inflated balloon of a desired size and shape which can readily be observed fluoroscopically when it is disposed within a patient. Liquid is preferred as an inflation fluid because it is relatively incompressible and ensures that the relatively inelastic balloon will be inflated to a predetermined size and shape. Upon inflation of the balloon, the prostatic urethra 32 and the surrounding prostate gland 38 are dilated thereby opening the partially occluded or totally occluded urethra for increased fluid flow therethrough.

After the dilatation of the prostatic urethra 32, the balloon 13 may be deflated and advanced into the patient's bladder so that the cystoscope 34 can be advanced through the prostatic urethra 32 while the physician is observing through eyepiece 37 to ascertain whether the dilatation was successful and whether there has been any damage thereto.

The flexible cystoscope 34 generally has a working channel 33 with an inner diameter of less than about 3 mm, usually less than 2.5 mm and the shaft of the catheter body 10 must therefore be small enough for the working channel 3 to slidably receive the shaft. Light is transmitted through fiber optic bundles 39 and 40 and observations are made through bundle 41. Suitable flexible cystoscopes include the CYF Flexible Cystoscope sold by the Olympus Corporation and the AFCI Flexible Cystoscope sold by the Circon Corp.

While the description of the present invention herein as been in terms of certain preferred embodiments, it should be apparent that various modifications can be made to the invention. For example, the dilatation balloon of the catheter is described herein as being secured to the catheter body passing therethrough by the proximal and distal skirts thereof. It should be recognized that the balloon can be an integral part of the catheter body. Other modifications and improvements can be made to the invention without departing from the scope thereof.

What is claimed is:

1. A catheter system for dilating a prostatic urethra, comprising:
   (a) a cystoscope having an elongated tubular body whereby said cystoscope is dimensioned to be advanced through a patient's urethra, said elongated tubular body including proximal and distal ends and a working channel passing therethrough with an opening at the distal end thereof, and said cystoscope having observation means extending therethrough and means on the proximal end thereof to view an area adjacent the distal end thereof;
   (b) a dilatation catheter slidably disposed within the working channel of the cystoscope, the dilatation catheter having:
      (i) an elongated catheter shaft less than 100 cm in length and less than 4 mm in diameter, and said catheter shaft having proximal and distal ends and an inner inflation lumen extending therein,
      (ii) a flexible, relatively inelastic balloon on a distal portion of the elongated catheter shaft, said balloon having an interior in fluid communication with the inner inflation lumen of the elongated catheter shaft, and said balloon having an inflated diameter between about 15 and about 50 mm whereby said balloon is inflatable to dilate a prostatic urethra,
      (iii) a core member disposed within the inflation lumen of the elongated catheter shaft, said core member is fixed within the catheter to prevent longitudinal movement thereof and to facilitate advancing the distal portion of the catheter shaft having the balloon thereon within a stenosed prostatic urethra, said core member extending through the distal end of the elongated catheter shaft and a flexible body disposed around and secured to the portion of the core member which extends through the distal end of the catheter shaft, and said core member being dimensioned along its length to increase the flexibility of the catheter, and
      (iv) means on the proximal end of the catheter shaft to direct inflation fluid to the interior of the balloon through the inner lumen of the elongated catheter shaft, said means to direct inflation fluid including a length of hypotubing at the proximal end of the catheter shaft wherein the proximal end of the core member is secured to the length of hypotubing without occluding the inner lumen of the catheter shaft; and
   (c) wherein said dilatation catheter may be advanced through a patient's urethra and the inflatable balloon positioned within the prostatic urethra distal to the external urethral sphincter thereof, and inflation fluid may be directed through the inner lumen of the catheter shaft into the interior of the balloon to inflate the balloon and thereby dilate the prostatic urethra.

2. The catheter system of claim 1 wherein the core member extends out the distal end of the catheter shaft and a flexible member located on the portion of the core member extending out of the catheter shaft and wherein the flexible member extends into a patient's bladder when the balloon is positioned within the patient's prostatic urethra.

3. The catheter system of claim 2 wherein the balloon is secured by the proximal and distal ends thereof to the catheter shaft which extends therethrough and wherein the maximum diameter of the catheter shaft proximal to the balloon is less than about 3 mm so as to be slidable within the working channel of the cystoscope.

4. The catheter system of claim 3 wherein the flexible member on the portion of the core member that extends out of the catheter shaft is a helical coil and wherein the helical coil has a proximal end secured to the distal end of the catheter shaft and said helical coil has a distal end secured to the core member.

* * * * *